(12) United States Patent
El Qacemi et al.

(10) Patent No.: US 9,320,278 B2
(45) Date of Patent: Apr. 26, 2016

(54) METHODS OF CONTROLLING INSECTS

(71) Applicant: Syngenta Participations AG, Basel (CH)

(72) Inventors: Myriem El Qacemi, Stein (CH); Jerome Yves Cassayre, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/421,878

(22) PCT Filed: Aug. 16, 2013

(86) PCT No.: PCT/EP2013/067186
§ 371 (c)(1),
(2) Date: Feb. 16, 2015

(87) PCT Pub. No.: WO2014/029709
PCT Pub. Date: Feb. 27, 2014

(65) Prior Publication Data
US 2015/0216169 A1 Aug. 6, 2015

(30) Foreign Application Priority Data

| Aug. 24, 2012 | (EP) | ................................. | 12181768 |
| Nov. 30, 2012 | (EP) | ................................. | 12195020 |
| Aug. 14, 2013 | (EP) | ................................. | 13180405 |

(51) Int. Cl.
*A01N 43/80* (2006.01)
*C07D 261/04* (2006.01)
*G06Q 30/00* (2012.01)

(52) U.S. Cl.
CPC .............. *A01N 43/80* (2013.01); *C07D 261/04* (2013.01); *G06Q 30/018* (2013.01)

(58) Field of Classification Search
CPC .................................................... A01N 43/80
USPC ........................................................ 514/380
See application file for complete search history.

(56) References Cited

FOREIGN PATENT DOCUMENTS

| WO | 2011067272 | 6/2011 |
| WO | 2013050302 | 4/2013 |

OTHER PUBLICATIONS

International Search Report for International Patent Application No. PCT/EP2013/067186 mailed Oct. 2, 2013.

*Primary Examiner* — Taofiq A Solola
(74) *Attorney, Agent, or Firm* — R. Kody Jones

(57) ABSTRACT

The present invention relates to methods, preferably for controlling and/or preventing infestation of boll weevil in cotton, comprising applying to a crop of cotton plants, the locus thereof, or propagation material thereof, a compound of formula (I), wherein $-B^1-B^2-B^3-$ is $-C=N-O-$, $-C=N-CH_2-$, $-C=CH-O-$ or $-N-CH_2-CH_2-$; L is a direct bond or methylene; $A^1$ and $A^2$ are C—H, or one of $A^1$ and $A^2$ is C—H and the other is N; $X^1$ is group X $R^1$ is $C_1$-$C_4$alkyl, $C_1$-$C_4$aloalkyl or $C_3$-$C_6$cycloalkyl; $R^2$ is chlorodifluoromethyl or trifluoromethyl; each $R^3$ is independently bromo, chloro, fluoro or trifluoromethyl; $R^4$ is hydrogen, halogen, methyl, halomethyl or cyano; $R^5$ is hydrogen; or $R^4$ and $R^5$ together form a bridging 1,3-butadiene group; p is 2 or 3.

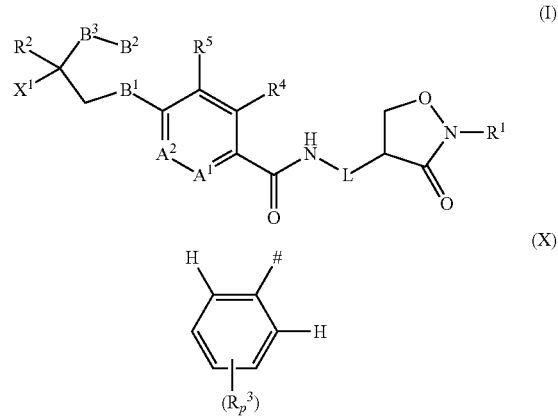

5 Claims, No Drawings

METHODS OF CONTROLLING INSECTS

RELATED APPLICATION INFORMATION

This application is a 371 of International Application No. PCT/EP2013/067186, filed 16 Aug. 2013, which claims priority to EP Patent Application No. 12181768.8 filed 24 Aug. 2012; EP Patent Application No. 12195020.8 filed 30 Nov. 2012; and EP Patent Application No. 13180405.6 filed 14 Aug. 2013, the contents of which are incorporated herein by reference.

The present invention relates to a method of controlling insects, in particular insects of the family Curculionidae, and in particular in cotton.

Insects of the Curculionidae family (commonly known as weevils) are almost entirely plant feeders. Several members of this family, in particular members of the genus *Anthonomus*, are known to be important agronomic pests in a variety of commercially important flowering crops and flowering ornamental plants. Weevils are known to attack, inter alia, cotton, apple, hazelnut, oil seed rape, strawberry and pepper crops.

Benchmark active ingredients which have so far been used to control members of the Curculionidae, in particular *Anthonomus*, suffer several disadvantages. One of these, endosulfan, has been banned in over 80 countries due to its threat to human health and the environment. Pyrethroids such as cyfluthrin and betacyfluthrin are less effective now due to the appearance of resistance. Thus, there is a clear need to find insecticides which can be used to control Curculionidae, in particular *Anthonomus*.

Compounds that are insecticidally, acaricidally, nematicidally and/or moluscicidally active by antagonism of the gamma-aminobutyric acid (GABA)-gated chloride channel, and which comprise a partially saturated heterocycle that is substituted by a haloalkyl substituent and one or two optionally substituted aromatic or heteroaromatic rings, represent a new class of pesticides that are described for example in Ozoe et al. Biochemical and Biophysical Research Communications, 391 (2010) 744-749. Compounds from this class are broadly described in WO 2005/085216 (EP1731512), WO 2007/123853, WO 2007/075459, WO2009/002809, WO 2008/019760, WO 2008/122375, WO 2008/128711, WO 2009/097992, WO 2010/072781, WO 2010/072781, WO 2008/126665, WO 2007/125984, WO 2008/130651, JP2008110971, JP2008133273, JP2009108046, WO 2009/022746, WO 2009/022746, WO 2010/032437, WO 2009/080250, WO 2010/020521, WO 2010/025998, WO 2010/020522, WO 2010/084067, WO 2010/086225, WO 2010/149506 and WO 2010/108733.

It has now surprisingly been found that particular insecticides from this new class of gamma-aminobutyric acid (GABA)-gated chloride channel antagonists (disclosed in e.g. WO 2011/067272) are highly effective at controlling *Anthonomus*.

These compounds therefore represent an important new solution for safeguarding crops of useful plants, particularly cotton crops, from insects from the family Curculionidae, particularly where the insects are resistant to current methods.

In a first aspect the invention provides a method comprising applying to a crop of cotton plants, the locus thereof, or propagation material thereof, a compound of formula I

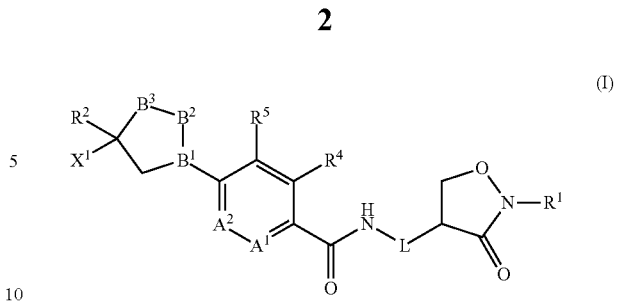

wherein
-B$^1$-B$^2$-B$^3$- is —C=N—O—, —C=N—CH$_2$—, —C=CH—O— or —N—CH$_2$—CH$_2$—;
L is a direct bond or methylene;
A$^1$ and A$^2$ are C—H, or one of A$^1$ and A$^2$ is C—H and the other is N;
X$^1$ is group X

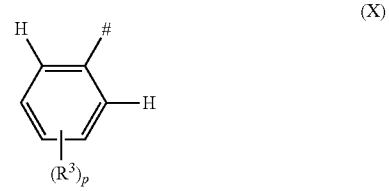

R$^1$ is C$_1$-C$_4$alkyl, C$_1$-C$_4$haloalkyl or C$_3$-C$_6$cycloalkyl;
R$^2$ is chlorodifluoromethyl or trifluoromethyl;
each R$^3$ is independently bromo, chloro, fluoro or trifluoromethyl;
R$^4$ is hydrogen, halogen, methyl, halomethyl or cyano;
R$^5$ is hydrogen;
or R$^4$ and R$^5$ together form a bridging 1,3-butadiene group;
p is 2 or 3.

In a further aspect the invention provides a method of controlling and/or preventing infestation of insects of the family Curculionidae in cotton comprising applying to a crop of cotton plants, the locus thereof, or propagation material thereof, a compound that of formula I. The insects of the family Curculionidae may be those that are resistant to one or more other insecticides.

In a further aspect the invention provides a method of controlling and/or preventing infestation of insects of the family Curculionidae in a crop of useful plants comprising applying to a crop of useful plants, the locus thereof, or propagation material thereof, a compound of formula I. The insects of the family Curculionidae may be those that are resistant to one or more other insecticides.

In a further aspect the invention provides use of a compound of formula I for control of insects of the family Curculionidae in useful plants. The use may be for controlling Curculionidae that are resistant to one or more other insecticides.

In a further aspect the invention provides a method of controlling and/or preventing infestation of *Anthonomus grandis* in a crop of useful plants comprising applying to a crop of useful plants, the locus thereof, or propagation material thereof, a compound of formula I. The *Anthonomus grandis* may be those that are resistant to one or more other insecticides.

In a further aspect the invention provides use of a compound of formula I for control of *Anthonomus grandis* in useful plants. The use may be for controlling *Anthonomus grandis* that are resistant to one or more other insecticides.

In a further aspect the invention provides a method of controlling and/or preventing infestation of *Anthonomus grandis* in a crop of cotton comprising applying to a crop of cotton, the locus thereof, or propagation material thereof, a compound of formula I. The *Anthonomus grandis* may be those that are resistant to one or more other insecticides.

In a further aspect the invention provides use of a compound of formula I for control of *Anthonomus grandis* in cotton. The use may be for controlling *Anthonomus grandis* that are resistant to one or more other insecticides.

Protection of a crop in a plot can be achieved by applying one or more pesticides to only a designated area of the plot. The designated part of the plot is usually the outer most part of the plot, and is generally a border area of sufficient size that penetration of the insects/pests is prevented to the remaining part of the plot. The benefit of spraying the border areas of the plot include a greater ability to control pest infestation because said insects/pests predominantly approach the plot from the periphery of the plot (i.e. from the sides of the plot). There is also the benefit that a lower volume of active ingredient could be applied whilst still controlling the insects/pests pressure for the entire plot. Therefore, the designated plot part forms an outer border of the plot, which can uniformly encompass the remaining plot, but embodiments wherein the border is not uniform and wherein the border doesn't completely encompass the remaining plot is also envisaged provided the said insects/pests are controlled to an acceptable level in the plot. Further, the designated plot part doe not have to form the outer most part of the plot, but that is preferred to minimize the crop damage by the said insects/pests. The area of the designated plot is of such size that acceptable control of the insects/pests is achieved. A skilled person would understand that a plot containing a crop would be applied with a number of pesticides during its growth. The application of the pesticides to a designated plot can be applicable to all pesticide application, but would be more appropriate to those pesticides controlling those insects/pests that predominantly approach the plot from the periphery of the plot; accordingly, the remaining pesticides would be applied as normal, for example, throughout the plot. For example, pesticide A is for control of insects/pests that pests that predominantly approach the plot from the periphery of the plot while pesticide B is broad spectrum fungicide; therefore, pesticide A & B, either simultaneously or in any sequence, would be applied to the designated plot part (i.e. a border region), while pesticide B would applied be applied throughout the plot.

Accordingly, in a further aspect, the invention provides a method of protecting a plot of at least five hectares comprising a crop of useful plants, preferably cotton, susceptible to and/or under attack by insects/pests, preferably of the family Curculionidae, said method comprising applying to said plant and/or said insects/pests a compound of formula I in a predefined plot part that is between 0.5 to 20%, based on area, of the plot, provided said pre-defined plot part forms the outer border of the plot, wherein said insects/pests predominantly approach the plot from the periphery of the plot.

In a preferred embodiment, the pre-defined plot part that is applied with a compound of formula I is between 1 to 20%, based on area, of the plot, especially 5 to 15%. In an embodiment, the plot is between 5 to 10,000, such as at most 50 to 5,000, especially 100 to 1,000, particularly 150 to 500, hectares.

In a further aspect the invention provides a method for obtaining regulatory approval for the use of one or more of a compound of formula I to control, preferably in cotton, an insect of the family Curculionidae, in particular the species *Anthonomus grandis, Conotrachelus nenuphar, Ceutorhynchus* spp., or *Curculio nucum*, preferably *Anthonomus grandis*, comprising at least one step of referring to, submitting or relying on biological data showing that said active ingredient reduces insect pressure.

The compounds of formula (I) may exist in different geometric or optical isomers or tautomeric forms. This invention covers all such isomers and tautomers and mixtures thereof in all proportions as well as isotopic forms such as deuterated compounds. The invention also covers salts and N-oxides of the compounds of the invention.

Alkyl groups (either alone or as part of a larger group, such as alkoxy-, alkylthio-, alkylsulfinyl-, alkylsulfonyl-, alkylcarbonyl- or alkoxycarbonyl-) can be in the form of a straight or branched chain and are, for example, methyl, ethyl, propyl, prop-2-yl, butyl, but-2-yl, 2-methyl-prop-1-yl or 2-methyl-prop-2-yl. The alkyl groups are preferably $C_1$-$C_6$, more preferably $C_1$-$C_4$, most preferably $C_1$-$C_3$ alkyl groups. Where an alkyl moiety is said to be substituted, the alkyl moiety is preferably substituted by one to four substituents, most preferably by one to three substituents.

Halogen is fluorine, chlorine, bromine or iodine.

Haloalkyl groups are alkyl groups which are substituted by one or more of the same or different halogen atoms and are, for example, difluoromethyl, trifluoromethyl, chlorodifluoromethyl or 2,2,2-trifluoro-ethyl.

Preferred substituent definitions are described below and may be combined in any combination, including with original definitions.

-$B^1$-$B^2$-$B^3$- is preferably —C═N—O—.

$A^1$ and $A^2$ are preferably C—H.

Preferably $X^1$ is 3,5-dichlorophenyl-, 3-chloro-4-fluorophenyl-, 3-fluoro-4-chlorophenyl-, 3,4-dichlorophenyl-, 3-chloro-4-bromophenyl-, 3,5-dichloro-4-fluorophenyl-, 3,4,5-trichlorophenyl-, 3,4,5-trifluorophenyl-, 3-chloro-5-bromophenyl-, 3-chloro-5-fluorophenyl-, 3-chloro-5-(trifluoromethyl)phenyl-, 3,4-dichloro-5-(trifluoromethyl)phenyl-, 3,5-bis(trifluoromethyl)phenyl-, 4-chloro-3,5-bis(trifluoromethyl)phenyl-, 3-(trifluoromethyl)phenyl-, more preferably 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 3,5-dichloro-4-bromophenyl-, 3-bromo-5-(trifluoromethyl)phenyl-, 3,5-dibromophenyl-, or 3,4-dichlorophenyl-, even more preferably 3,5-dichloro-phenyl, 3,5-dichloro-4-fluorophenyl-, 3,4,5-trichlorophenyl-, 3,5-bis(trifluoromethyl)phenyl, most preferably $R^4$ is 3,5-dichlorophenyl.

$R^1$ is preferably methyl, ethyl, propyl, butyl, cyclopropyl, cyclobutyl, trifluoroethyl, difluoroethyl. Ethyl and trifluoroethyl are particularly preferred.

$R^2$ is preferably trifluoromethyl.

Preferably each $R^3$ is independently chlorine or fluorine, most preferably chlorine.

$R^4$ is preferably chloro or methyl, most preferably methyl.

$R^5$ is preferably hydrogen.

L is preferably a direct bond.

In one group of compounds -$B^1$-$B^2$-$B^3$- is —C═N—O—.

In one group of compounds -$B^1$-$B^2$-$B^3$- is —C═N—$CH_2$—.

In one group of compounds -$B^1$-$B^2$-$B^3$- is —C═CH—O—.

In one group of compounds -$B^1$-$B^2$-$B^3$- is —N—$CH_2$—$CH_2$—.

In one embodiment $A^1$ and $A^2$ are C—H, $R^2$ is trifluoromethyl, and $R^5$ is hydrogen.

In one embodiment $A^1$ and $A^2$ are C—H, $R^2$ is trifluoromethyl, $R^5$ is hydrogen and L is a direct bond.

In one embodiment -B$^1$-B$^2$-B$^3$- is —C=N—O—, A$^1$ and A$^2$ are C—H, R$^2$ is trifluoromethyl, R$^5$ is hydrogen and L is a direct bond.

In one embodiment -B$^1$-B$^2$-B$^3$- is —C=N—O—, A$^1$ and A$^2$ are C—H, R$^2$ is trifluoromethyl, R$^4$ is halogen or methyl, R$^5$ is hydrogen and L is a direct bond.

In one embodiment -B$^1$-B$^2$-B$^3$- is —C=N—O—, A$^1$ and A$^2$ are C—H, R$^2$ is trifluoromethyl, R$^3$ is chloro or fluoro, R$^4$ is halogen or methyl, R$^5$ is hydrogen and L is a direct bond.

In one embodiment A$^1$ and A$^2$ are C—H, R$^2$ is trifluoromethyl, R$^4$ is methyl, R$^5$ is hydrogen, each R$^3$ is chlorine, p is 2.

In one embodiment R$^1$ is C$_1$-C$_4$alkyl, e.g. methyl, ethyl or propyl, e.g. methyl or ethyl, e.g. ethyl.

In one embodiment X$^1$ is group Xa

Xa

In one embodiment R$^1$ is C$_1$-C$_8$alkyl, e.g. methyl, ethyl or propyl, e.g. methyl or ethyl, e.g. ethyl and X$^1$ is group Xa.

In one embodiment R$^1$ is methyl.

In one embodiment R$^1$ is ethyl.

In one embodiment R$^1$ is 2,2,2-trifluoroethyl.

In one embodiment R$^1$ is 2,2-difluoroethyl.

In one embodiment X$^1$ is 3,5-dichlorophenyl.

In one embodiment X$^1$ is 3,5-dichloro-4-fluorophenyl.

In one embodiment X$^1$ is 3,4,5-trichlorophenyl.

In one embodiment R$^1$ is methyl and X$^1$ is 3,5-dichlorophenyl.

In one embodiment R$^1$ is methyl and X$^1$ is 3,5-dichloro-4-fluorophenyl.

In one embodiment R$^1$ is methyl and X$^1$ is 3,4,5-trichlorophenyl.

In one embodiment R$^1$ is ethyl and X$^1$ is 3,5-dichlorophenyl.

In one embodiment R$^1$ is ethyl and X$^1$ is 3,5-dichloro-4-fluorophenyl.

In one embodiment R$^1$ is ethyl and X$^1$ is 3,4,5-trichlorophenyl.

In one embodiment R$^1$ is 2,2,2-trifluoroethyl and X$^1$ is 3,5-dichlorophenyl.

In one embodiment R$^1$ is 2,2,2-trifluoroethyl and X$^1$ is 3,5-dichloro-4-fluorophenyl.

In one embodiment R$^1$ is 2,2,2-trifluoroethyl and X$^1$ is 3,4,5-trichlorophenyl.

In one embodiment R$^1$ is 2,2-difluoroethyl and X$^1$ is 3,5-dichlorophenyl.

In one embodiment R$^1$ is 2,2-difluoroethyl and X$^1$ is 3,5-dichloro-4-fluorophenyl.

In one embodiment R$^1$ is 2,2-difluoroethyl and X$^1$ is 3,4,5-trichlorophenyl.

Compounds of formula I may exist as compounds of formula I* or compounds of formula I**.

(I*)

(I**)

Compounds of formula I** are more biologically active than compounds of formula I*. Compounds of formula I may be a mixture of compounds I* and I in any ratio e.g. in a molar ratio of 1:99 to 99:1, e.g. 10:1 to 1:10, e.g. a substantially 50:50 molar ratio. Preferably the compound of formula I is a racemic mixture of the compounds of formula I and I* or is enantiomerically enriched for the compound of formula I. For example, when the compound of formula I is an enantiomerically enriched mixture of formula I, the molar proportion of compound I compared to the total amount of both enantiomers is for example greater than 50%, e.g. at least 55, 60, 65, 70, 75, 80, 85, 90, 95, 96, 97, 98, or at least 99%. In one embodiment the compound of formula I is a compound of formula I in substantially pure form, e.g. it is provided substantially in the absence of the alternative enantiomer.

Compounds of formula I may also exist as compounds of formula I' or compounds of formula I".

(I')

(I")

(S=S stereochemistry, R=R stereochemistry, both corresponding to the stereochemistry when L is a direct bond)

Compounds of formula I" are often more biologically active than compounds of formula I'. The compound of formula I may be a mixture of compounds I' and I" in any ratio e.g. in a molar ratio of 1:99 to 99:1, e.g. 10:1 to 1:10, e.g. a substantially 50:50 molar ratio. Preferably the compound of formula I is a racemic mixture of the compounds of formula I" and I' or is enantiomerically enriched for the compound of formula I". For example, when the compound of formula I is an enantiomerically enriched mixture of formula I", the molar proportion of compound I" compared to the total amount of both enantiomers is for example greater than 50%, e.g. at least 55, 60, 65, 70, 75, 80, 85, 90, 95, 96, 97, 98, or at least 99%. In a preferred embodiment the compound of formula I is a compound of formula I" in substantially pure form, e.g. it is provided substantially in the absence of the alternative enantiomer.

The above stereocentres give rise to four stereoisomers:

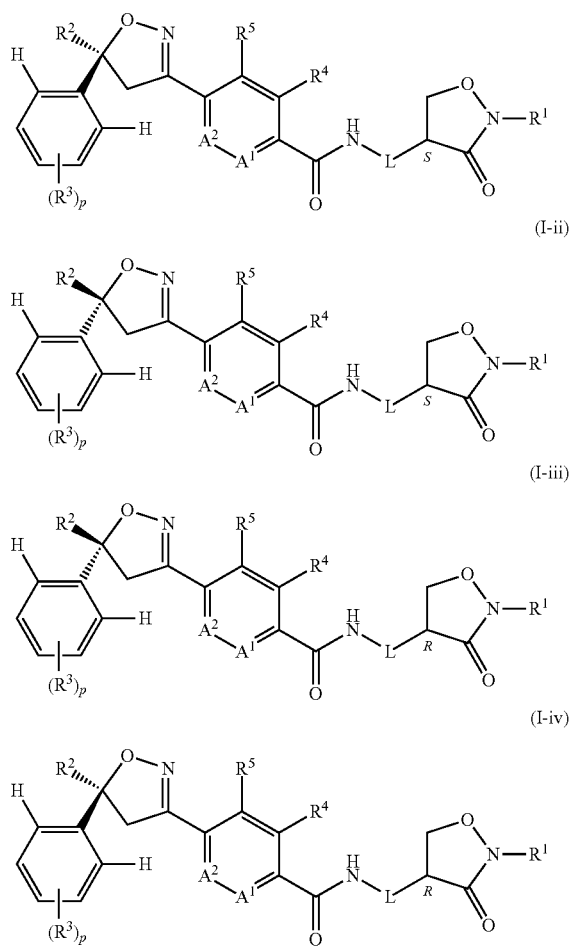

In one embodiment the compound of formula I is a mixture comprising compounds I-i, I-ii, I-iii and I-iv, wherein the mixture is enriched for the compound of formula I-iv, e.g. the molar proportion of compound I-iv compared to the total amount of the four isomers is for example greater than 25%, e.g. at least 30, 35, 40, 50, 55, 60, 65, 70, 75, 80, 85, 90, 95, 96, 97, 98, or at least 99%.

In another embodiment the compound of formula I is a mixture comprising compounds I-i, I-ii, I-iii and I-iv, wherein the molar amount of the compound of formula I-iv is greater than the molar amount of the compound of formula I-i, and the molar amount of the compound I-ii, and the molar amount of the compound of formula I-iii, in other words, the compound of formula I-iv is the most abundant isomer in the mixture. For example the molar amount of compound of formula I-iv is at least 1, 2, 5, 10, 15, 20, 25, 30, 35, 40, 45, 50, 55, 60, 56, 70, 75, 80, 85, 90, or even at least 95% greater than the combined amount of the compound of formula I-iv and I-i, the combined amount of the compound of formula I-iv and I-ii, and the combined amount of compound of formula I-iv and I-iii.

Although $B^1$-$B^2$-$B^3$ is shown above as C=N—O, the same applies in respect of the stereoisomers when $B^1$-$B^2$-$B^3$ is —C=N—CH$_2$—, —C=CH—O— and —N—CH$_2$—CH$_2$—.

In one embodiment the compound of formula I-iv is the most abundant isomer and $R^1$ is $C_1$-$C_4$alkyl, e.g. methyl, ethyl or propyl, e.g. methyl or ethyl, e.g. ethyl.

In one embodiment the compound of formula I-iv is the most abundant isomer and $R^1$ is $C_1$-$C_4$alkyl, e.g. methyl, ethyl or propyl, e.g. methyl or ethyl, e.g. ethyl and $X^1$ is group Xa.

In one embodiment the compound of formula I-iv is the most abundant isomer and $R^1$ is methyl.

In one embodiment the compound of formula I-iv is the most abundant isomer and $R^1$ is ethyl.

In one embodiment the compound of formula I-iv is the most abundant isomer and $R^1$ is 2,2,2-trifluoroethyl.

In one embodiment the compound of formula I-iv is the most abundant isomer and $R^1$ is 2,2-difluoroethyl.

Preferred compounds of formula I are shown in the Tables below.

TABLE A

Compounds of formula (I-a)

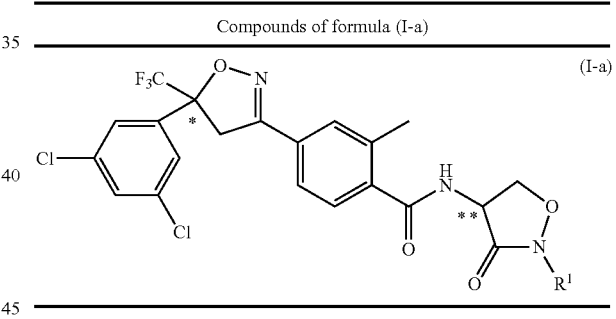

Table A provides 78 compounds and mixtures of formula (I-a) wherein $R^1$ has the values listed in table X below. The symbols * and ** indicate the location of the chiral centres.

TABLE B

Compounds of formula (I-b)

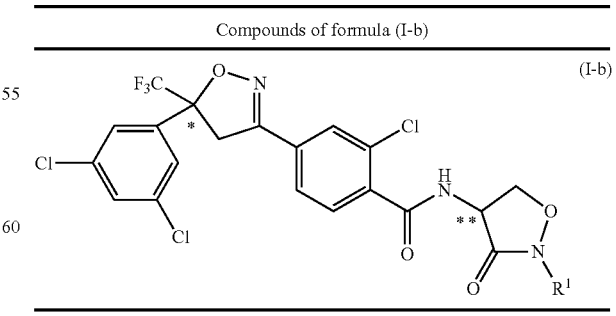

Table B provides 78 compounds and mixtures of formula (I-b) wherein $R^1$ has the values listed in table X below. The symbols * and ** indicate the location of the chiral centres.

TABLE C

Compounds of formula (I-c)

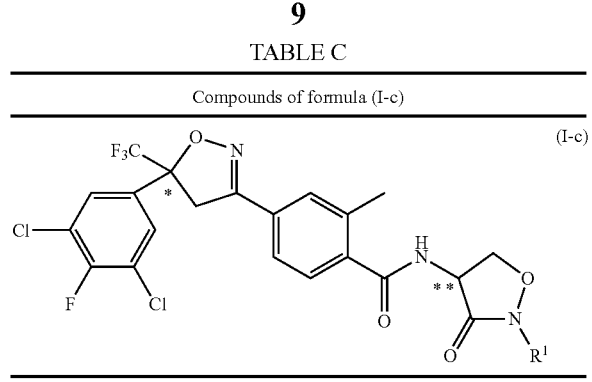

(I-c)

Table C provides 78 compounds and mixtures of formula (I-c) wherein $R^1$ has the values listed in table X below. The symbols * and ** indicate the location of the chiral centres.

TABLE D

Compounds of formula (I-d)

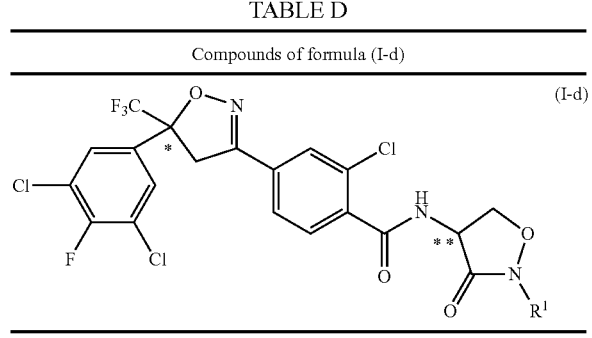

(I-d)

Table D provides 78 compounds and mixtures of formula (I-d) wherein $R^1$ has the values listed in table X below. The symbols * and ** indicate the location of the chiral centres.

TABLE E

Compounds of formula (I-e)

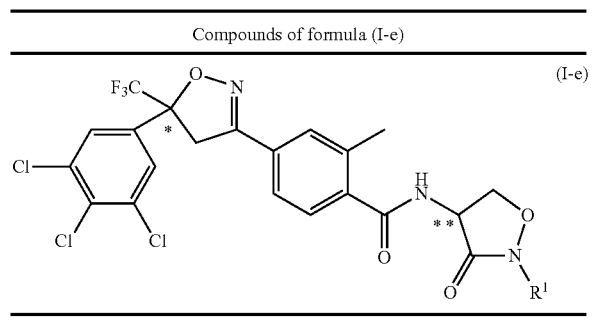

(I-e)

Table E provides 78 compounds and mixtures of formula (I-e) wherein $R^1$ has the values listed in table X below. The symbols * and ** indicate the location of the chiral centres.

TABLE F

Compounds of formula (I-f)

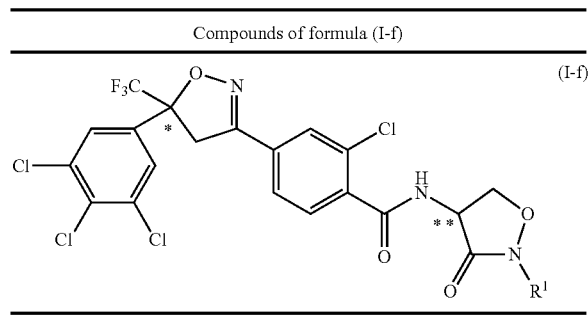

(I-f)

Table F provides 78 compounds and mixtures of formula (I-f) wherein $R^1$ has the values listed in table X below. The symbols * and ** indicate the location of the chiral centres.

Table X represents Table A when X is A, Table B when X is B, Table C when X is C, Table D when X is D, Table E when X is E, Table F when X is F.

| Compound numbers | Stereochemistry at * | Stereochemistry at ** | $R^1$ |
|---|---|---|---|
| X.1 | Racemic mixture | Racemic mixture | ethyl- |
| X.2 | Racemic mixture | Racemic mixture | butyl- |
| X.3 | Racemic mixture | Racemic mixture | but-2-yl- |
| X.4 | Racemic mixture | Racemic mixture | 3-bromo-propyl- |
| X.5 | Racemic mixture | Racemic mixture | 2,2,2-trifluoro-ethyl- |
| X.6 | Racemic mixture | Racemic mixture | 3,3,3-trifluoro-propyl- |
| X.7 | Racemic mixture | Racemic mixture | cyclobutyl- |
| X.8 | Racemic mixture | Racemic mixture | methyl |
| X.9 | Racemic mixture | Racemic mixture | propyl |
| X.10 | Racemic mixture | Racemic mixture | 2,2-difluoro-ethyl- |
| X.11 | Racemic mixture | Racemic mixture | 2-fluoro-ethyl- |
| X.12 | S | Racemic mixture | ethyl- |
| X.13 | S | Racemic mixture | butyl- |
| X.14 | S | Racemic mixture | but-2-yl- |
| X.15 | S | Racemic mixture | 3-bromo-propyl- |
| X.16 | S | Racemic mixture | 2,2,2-trifluoro-ethyl- |
| X.17 | S | Racemic mixture | 3,3,3-trifluoro-propyl- |
| X.18 | S | Racemic mixture | cyclobutyl- |
| X.19 | S | Racemic mixture | methyl |
| X.20 | S | Racemic mixture | propyl |
| X.21 | S | Racemic mixture | 2,2-difluoro-ethyl- |
| X.22 | S | Racemic mixture | 2-fluoro-ethyl- |
| X.23 | Racemic mixture | Racemic mixture | isopropyl |
| X.24 | Racemic mixture | Racemic mixture | cyclopropyl |
| X.25 | S | Racemic mixture | isopropyl |
| X.26 | S | Racemic mixture | cyclopropyl |
| X.27 | Racemic mixture | S | ethyl- |
| X.28 | Racemic mixture | S | butyl- |
| X.29 | Racemic mixture | S | but-2-yl- |
| X.30 | Racemic mixture | S | 3-bromo-propyl- |
| X.31 | Racemic mixture | S | 2,2,2-trifluoro-ethyl- |
| X.32 | Racemic mixture | S | 3,3,3-trifluoro-propyl- |
| X.33 | Racemic mixture | S | cyclobutyl- |
| X.34 | Racemic mixture | S | methyl |
| X.35 | Racemic mixture | S | propyl |
| X.36 | Racemic mixture | S | 2,2-difluoro-ethyl- |
| X.37 | Racemic mixture | S | 2-fluoro-ethyl- |
| X.38 | S | S | ethyl- |
| X.39 | S | S | butyl- |
| X.40 | S | S | but-2-yl- |
| X.41 | S | S | 3-bromo-propyl- |
| X.42 | S | S | 2,2,2-trifluoro-ethyl- |
| X.43 | S | S | 3,3,3-trifluoro-propyl- |
| X.44 | S | S | cyclobutyl- |
| X.45 | S | S | methyl |
| X.46 | S | S | propyl |
| X.47 | S | S | 2,2-difluoro-ethyl- |
| X.48 | S | S | 2-fluoro-ethyl- |
| X.49 | Racemic mixture | S | isopropyl |
| X.50 | Racemic mixture | S | cyclopropyl |
| X.51 | S | S | isopropyl |
| X.52 | S | S | cyclopropyl |
| X.53 | Racemic mixture | R | ethyl- |
| X.54 | Racemic mixture | R | butyl- |
| X.55 | Racemic mixture | R | but-2-yl- |
| X.56 | Racemic mixture | R | 3-bromo-propyl- |
| X.57 | Racemic mixture | R | 2,2,2-trifluoro-ethyl- |
| X.58 | Racemic mixture | R | 3,3,3-trifluoro-propyl- |
| X.59 | Racemic mixture | R | cyclobutyl- |
| X.60 | Racemic mixture | R | methyl |
| X.61 | Racemic mixture | R | propyl |
| X.62 | Racemic mixture | R | 2,2-difluoro-ethyl- |
| X.63 | Racemic mixture | R | 2-fluoro-ethyl- |
| X.64 | S | R | ethyl- |
| X.65 | S | R | butyl- |
| X.66 | S | R | but-2-yl- |
| X.67 | S | R | 3-bromo-propyl- |
| X.68 | S | R | 2,2,2-trifluoro-ethyl- |

-continued

| Compound numbers | Stereochemistry at * | Stereochemistry at ** | R¹ |
|---|---|---|---|
| X.69 | S | R | 3,3,3-trifluoro-propyl- |
| X.70 | S | R | cyclobutyl- |
| X.71 | S | R | methyl |
| X.72 | S | R | propyl |
| X.73 | S | R | 2,2-difluoro-ethyl- |
| X.74 | S | R | 2-fluoro-ethyl- |
| X.75 | Racemic mixture | R | isopropyl |
| X.76 | Racemic mixture | R | cyclopropyl |
| X.77 | S | R | isopropyl |
| X.78 | S | R | cyclopropyl |

The compounds of the invention may be made by a variety of methods as shown in Schemes 1 to 3.

Scheme 1

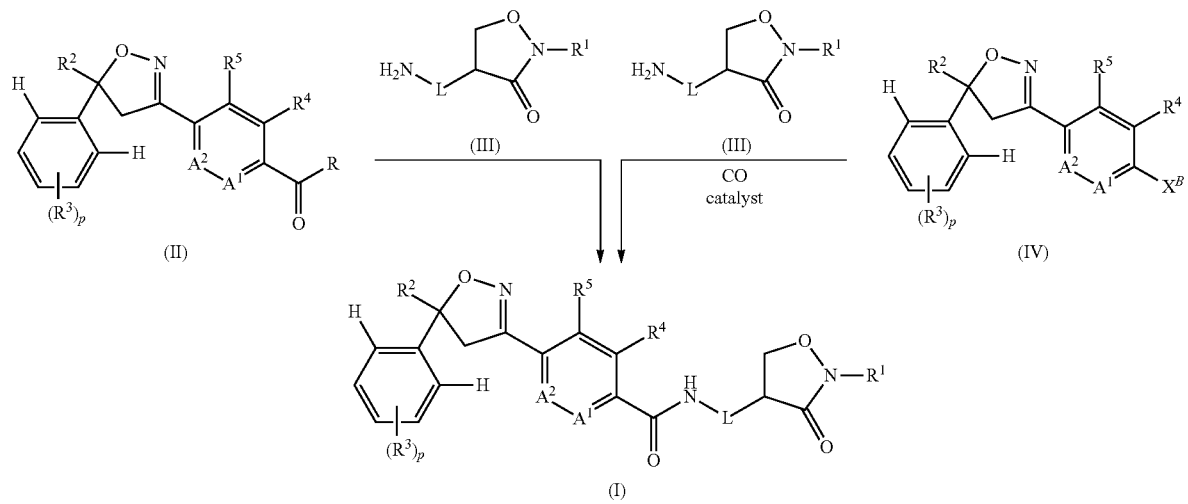

1) Compounds of formula (I), can be prepared by reacting a compound of formula (II) wherein R is OH, $C_1$-$C_6$alkoxy or Cl, F or Br, with an amine of formula (III) as shown in Scheme 1. When R is OH such reactions are usually carried out in the presence of a coupling reagent, such as N,N'-dicyclohexylcarbodiimide ("DCC"), 1-ethyl-3-(3-dimethylamino-propyl)carbodiimide hydrochloride ("EDC") or bis(2-oxo-3-oxazolidinyl)phosphonic chloride ("BOP-Cl"), in the presence of a base, and optionally in the presence of a nucleophilic catalyst, such as hydroxybenzotriazole ("HOBT"). When R is Cl, such reactions are usually carried out in the presence of a base, and optionally in the presence of a nucleophilic catalyst. Alternatively, it is possible to conduct the reaction in a biphasic system comprising an organic solvent, preferably ethyl acetate, and an aqueous solvent, preferably a solution of sodium hydrogen carbonate. When R is $C_1$-$C_6$alkoxy it is sometimes possible to convert the ester directly to the amide by heating the ester and amine together in a thermal process. Suitable bases include pyridine, triethylamine, 4-(dimethylamino)-pyridine ("DMAP") or diisopropylethylamine (Hunig's base). Preferred solvents are N,N-dimethylacetamide, tetrahydrofuran, dioxane, 1,2-dimethoxyethane, ethyl acetate and toluene. The reaction is carried out at a temperature of from 0° C. to 100° C., preferably from 15° C. to 30° C., in particular at ambient temperature. Amines of formula (III) are either known in the literature or can be prepared using methods known to a person skilled in the art.

2) Acid halides of formula (II), wherein R is Cl, F or Br, may be made from carboxylic acids of formula (II), wherein R is OH, under standard conditions, as described for example in WO 2009/080250.

3) Carboxylic acids of formula (II), wherein R is OH, may be formed from esters of formula (II), wherein R is $C_1$-$C_6$alkoxy as described for example in WO 2009/080250.

4) Compounds of formula (I) can be prepared by reacting a compound of formula (IV) wherein $X^B$ is a leaving group, for example a halogen, such as bromo, with carbon monoxide and an amine of formula (III), in the presence of a catalyst, such as palladium(II) acetate or bis-(triphenylphosphine)palladium(II) dichloride, optionally in the presence of a ligand, such as triphenylphosphine, and a base, such as sodium carbonate, pyridine, triethylamine, 4-(dimethylamino)-pyridine ("DMAP") or diisopropylethylamine (Hunig's base), in a solvent, such as water, N,N-dimethylformamide or tetrahydrofuran. The reaction is carried out at a temperature of from 50° C. to 200° C., preferably from 100° C. to 150° C. The reaction is carried out at a pressure of from 50 to 200 bar, preferably from 100 to 150 bar.

5) Compounds of formula (IV) wherein $X^B$ is a leaving group, for example a halogen, such as bromo, can be made by various methods, for example as described in WO 2009/080250.

Scheme 2

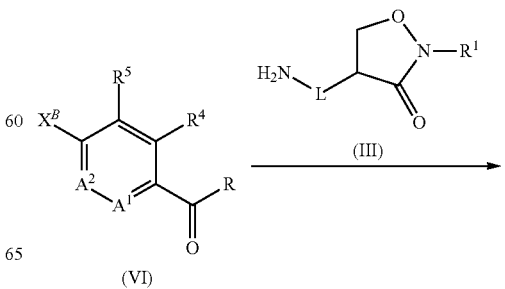

-continued

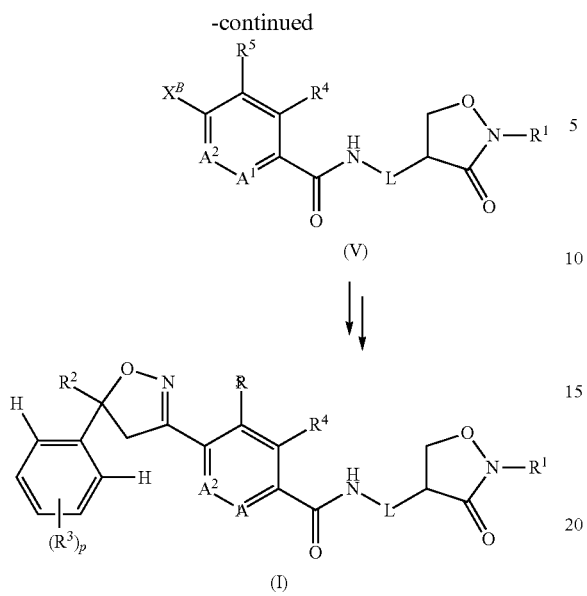

6) Alternatively, compounds of formula (I), can be prepared by various methods from an intermediate of formula (V) as shown in Scheme 2 wherein $X^B$ is a leaving group, for example a halogen, such as bromo, or $X^B$ is cyano, formyl or acetyl according to similar methods to those described in WO09080250. An intermediate of formula (V) can be prepared for example from an intermediate of formula (VI) as described in the same reference.

Scheme 3

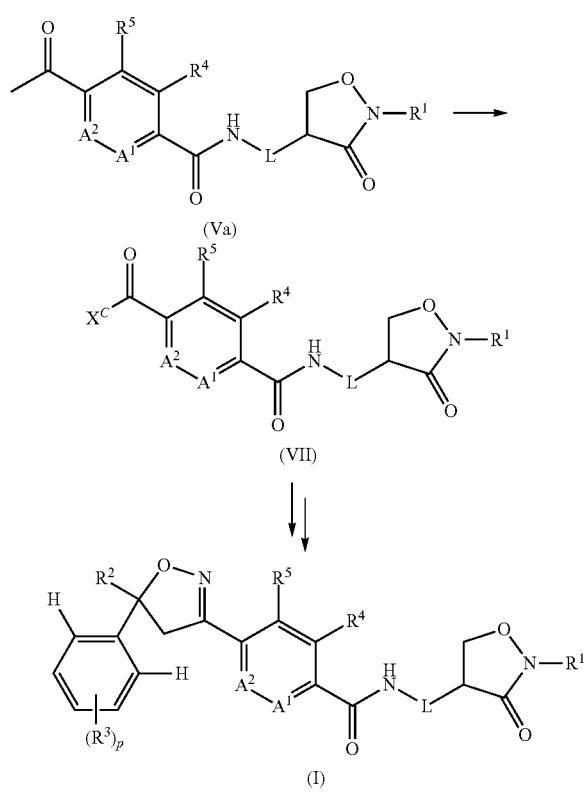

7) Alternatively, compounds of formula (I) can be prepared by various methods from an intermediate of formula (VII) as shown in Scheme 3 wherein $X^C$ is $X^C$-1 or $X^C$-2

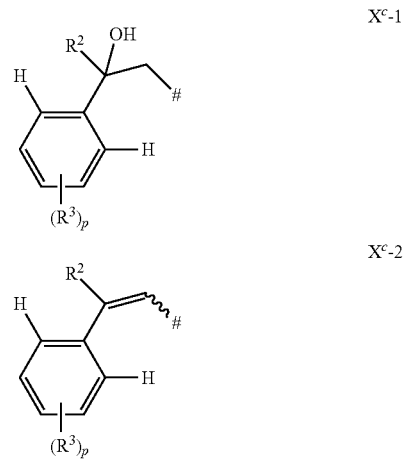

according to similar methods to those described in WO 2009/080250.

8) Compounds of formula (VII) wherein $X^C$ is $X^C$ is $X^C$-1 or $X^C$-2 can be prepared from a compound of formula (Va) from a compound of formula (VII) wherein $X^C$ is CH$_2$-halogen using similar methods to those described in WO 2009/080250.

9) Compounds of formula (VII) wherein $X^C$ is CH$_2$-halogen, such as bromo or chloro, can be prepared by reacting a methyl ketone of formula (Va) with a halogenating agent, such as bromine or chlorine, in a solvent, such as acetic acid, at a temperature of from 0° C. to 50° C., preferably from ambient temperature to 40° C.

Other methods for the preparation of compounds of formula I are described in PCT/EP2010/068605, which is incorporated herein by reference.

In one embodiment the invention provides a compound selected from Tables A to F for use against insects of the family Curculionidae, preferably in for use against *Anthonomus grandis*.

In one embodiment the invention provides a compound selected from Tables A to F for use against *Anthonomus grandis* in cotton.

Examples of insects from the family of Curculionidae are *Anthonomus corvulus, Anthonomus elutus, Anthonomus elongatus, Anthonomus eugenii, Anthonomus consors, Anthonomus haematopus, Anthonomus lecontei, Anthonomus molochinus, Anthonomus morticinus, Anthonomus musculus, Anthonomus nigrinus, Anthonomus phyllocola, Anthonomus pictus, Anthonomus pomorum, Anthonomus quadrigibbus, Anthonomus rectirostris, Anthonomus rubi, Anthonomus santacruzi, Anthonomus signatus, Anthonomus subfasciatus,* and *Anthonomus tenebrosus*. Preferably the insects from the family of Curculionidae are of the genus *Anthonomus*, preferably of the species *Anthonomus grandis, Conotrachelus nenuphar, Ceutorhynchus* spp., or *Curculio nucum*, more preferably of the species *Anthonomus grandis*.

In one embodiment the methods and uses of the invention are for controlling and/or preventing infestation of a cotton crop by *Anthonomus grandis* (commonly known as boll weevil) including *Anthonomus grandis* that is resistant to other insecticides, e.g. pyrethroid insecticides. *Anthonomus grandis* that is "resistant" to a particular insecticide refers e.g. to strains of *Anthonomus grandis* that are less sensitive to that insecticide compared to the expected sensitivity of the same species of *Anthonomus grandis*. The expected sensitivity can be measured using e.g. a strain that has not previously been exposed to the insecticide.

In another embodiment the compounds of the invention may be used on cotton to control, for example, *Anthonomus grandis, Pectinophora* spp., *heliothis* spp., *Spodoptera* spp., *Tetranychus* spp., *Empoasca* spp., *Thrips* spp., *Bemisia tabaci, Trialeurodes* spp., *Aphids, Lygus* spp., *phyllophaga* spp., *Scaptocoris* spp., *Austroasca viridigrisea, Creontiades* spp., *Nezara* spp., *Piezodorus* spp., *Halotydeus destructor, Oxycaraenus hyalinipennis, Dysdercus cingulatus*. In particular, the compounds of the invention are used on cotton to control *Anthonomus grandis, Tetranychus* spp., *Empoasca* spp., *thrips* spp., *Lygus* spp., *phyllophaga* spp., *Scaptocoris* spp.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of a plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

Application may be before infestation or when the pest is present. Application of the compounds of the invention can be performed according to any of the usual modes of application, e.g. foliar, drench, soil, in furrow etc. However, control of *Anthonomus grandis* s is usually achieved by foliar application, which is the preferred mode of application according to the invention.

Application of the compounds of the invention is preferably to a crop of cotton plants, the locus thereof or propagation material thereof.

The compounds of the invention may be applied to plant parts. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds. Treatment according to the invention of the plants and plant parts with the active compounds can be carried out directly or by allowing the compounds to act on their surroundings, habitat or storage space by the customary treatment methods, for example by immersion, spraying, evaporation, fogging, scattering, painting on, injecting and, in the case of propagation material, in particular in the case of seed, also by applying one or more coats.

The compounds of the invention are suitable for use on any plant (preferably cotton plant), including those that have been genetically modified to be resistant to active ingredients such as herbicides, or to produce biologically active compounds that control infestation by plant pests.

The term "plant" as used herein includes seedlings, bushes and trees. Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Compounds of formula I may be used on transgenic plants (including cultivars) obtained by genetic engineering methods and/or by conventional methods. These are understood as meaning plants having novel properties ("traits") which have been obtained by conventional breeding, by mutagenesis or by recombinant DNA techniques. Depending on the plant species or plant cultivars, their location and growth conditions (soils, climate, vegetation period, diet), the treatment according to the invention may also result in superadditive "synergistic") effects.

Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The preferred transgenic plants or plant cultivars which are to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products.

Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds.

Examples of transgenic plants which may be mentioned are the important crop plants, such as cereals (wheat, rice), maize, soybean, potatoes, sugar beet, tomatoes, peas and other vegetable varieties, cotton, tobacco, oilseed rape and also fruit plants (with the fruits apples, pears, citrus fruits and grapes). Transgenic cotton is of particular interest.

Compounds of formula I may be used on transgenic plants that are capable of producing one or more pesticidal proteins which confer upon the transgenic plant tolerance or resistance to harmful pests, e.g. insect pests, nematode pests and the like. Such pesticidal proteins include, without limitation, Cry proteins from *Bacillus thuringiensis* Cry1Ab, Cry1Ac, Cry1F, Cry2Ab, Cry2Ae, Cry3A, Cry3Bb, or Cry9C; engineered proteins such as modified Cry3A (U.S. Pat. No. 7,030,295) or Cry1A.105; or vegetative insecticidal proteins such as Vip1, Vip2 or Vip3. A full list of Bt Cry proteins and VIPs useful in the invention can be found on the worldwide web at

*Bacillus thuringiensis* Toxin Nomenclature Database maintained by the University of Sussex (see also, Crickmore et al. (1998) *Microbiol. Mol. Biol. Rev.* 62:807-813). Other pesticidal proteins useful in the invention include proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. Further examples of such pesticidal proteins or transgenic plants capable of synthesizing such proteins are disclosed, e.g., in EP-A 374753, WO 93/007278, WO 95/34656, EP-A 427529, EP-A 451878, WO 03/18810 and WO 03/52073. The methods for producing such transgenic plants are generally known to the person skilled in the art and some of which are commercially available such as Agrisure®CB (P1) (corn producing Cry1Ab), Agrisure®RW (P2) (corn producing mCry3A), Agrisure® Viptera (P3) (corn hybrids producing Vip3Aa); Agrisure300GT (P4) (corn hybrids producing Cry1Ab and mCry3A); YieldGard® (P5) (corn hybrids producing the Cry1Ab protein), YieldGard® Plus (P6) (corn hybrids producing Cry1Ab and Cry3Bb1), Genuity® SmartStax® (P7) (corn hybrids with Cry1A.105, Cry2Ab2, Cry1F, Cry34/35, Cry3Bb); Herculex® I (P8) (corn hybrids producing Cry1Fa) and Herculex®RW (P9) (corn hybrids producing Cry34Ab1, Cry35Ab1 and the enzyme Phosphinothricin-N-Acetyltransferase [PAT]); NuCOTN®33B (P10) (cotton cultivars producing Cry1Ac), Bollgard®I (P11) (cotton cultivars producing Cry1Ac), Bollgard®II (P12) (cotton cultivars producing Cry1Ac and Cry2Ab2) and VIPCOT® (P13) (cotton cultivars producing a Vip3Aa). Soybean Cyst Nematode resistance soybean (SCN®—Syngenta (P14)) and soybean with Aphid resistant trait (AMT® (P15)) are also of interest.

Further examples of such transgenic crops are:

1. Bt11 Maize from Syngenta Seeds SAS, Chemin de l'Hobit 27, F-31 790 St. Sauveur, France, registration number C/FR/96/05/10 (P16). Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10 (P17). Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10 (P18). Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9 (P19). MON 863 expresses a CryIIIB(b1) toxin and has resistance to certain Coleoptera insects.

5. IPC 531 Cotton from Monsanto Europe S.A. 270-272 Avenue de Tervuren, B-1150 Brussels, Belgium, registration number C/ES/96/02. (P20)

6. 1507 Maize from Pioneer Overseas Corporation, Avenue Tedesco, 7 B-1160 Brussels, Belgium, registration number C/NL/00/10. (P21) Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain Lepidoptera, include the European corn borer.

Further examples of transgenic plants, and of very high interest, are those carrying traits conferring resistance to 2.4D (e.g. Enlist®) (e.g. WO 2011066384) (glyphosate (e.g. Roundup Ready® (P24), Roundup Ready 2 Yield® (P25)), sulfonylurea (e.g. STS®) (P26), glufosinate (e.g. Liberty Link® (P27), Ignite® (P28)), Dicamba (P29) (Monsanto), HPPD tolerance (P30) (e.g. isoxaflutole herbicide) (Bayer CropScience, Syngenta). Double or triple stacks of any of the traits described here are also of interest, including glyphosate and sulfonyl-urea tolerance ((e.g. Optimum GAT®) (P31), plants stacked with STS® and Roundup Ready® (P32) or plants stacked with STS® and Roundup Ready 2 Yield® (P33)), dicamba and glyphosate tolerance (P34) (Monsanto). Of particular interest are soybean plants carrying trains conferring resistance to 2.4D (e.g. Enlist®), glyphosate (e.g. Roundup Ready®, Roundup Ready 2 Yield®), sulfonylurea (e.g. STS®), glufosinate (e.g. Liberty Link®, Ignite®), Dicamba (Monsanto) HPPD tolerance (e.g. isoxaflutole herbicide) (Bayer CropScience, Syngenta).

Transgenic crops of insect-resistant plants are also described in BATS (Zentrum für Biosicherheit and Nachhaltigkeit, Zentrum BATS, Clarastrasse 13, 4058 Basel, Switzerland) Report 2003, (http://bats.ch).

Examples of cotton transgenic events include MON 531/757/1076 (Bollgard I®—Monsanto), MON1445 (Roundup Ready Cotton®—Monsanto), MON531×MON1445 (Bollgard I+RR®—Monsanto), MON15985 (Genuity Bollgard II Cotton®—Monsanto), MON88913 (Genuity RR FLEX Cotton®—Monsanto), MON15985—MON1445 (Genuity Bollgard II+RR FELX Cotton®—Monsanto), MON15983× MON88913 (Genuity Bollgard II+RR FLEX Cotton®—Monsanto), MON15985 (FibreMax Bollgard II Cotton®—Monsanto), LL25 (FibreMax LL Cotton®-BCS Stoneville), GHB614 (FibreMax GlyTol Cotton®-BCS Stoneville), LL25×MON15985 (FibreMax LL Bollgard II Cotton®—BCS Stoneville/Monsanto), GHB614×LL25 (FibreMax LL GlyTol Cotton®-BCS Stoneville), GHB614×LL25× MON15985 (FibreMax RR GlyTol Bollgard II Cotton®-BCS Stoneville), MON88913×MON15985 (FibreMax LL GlyTol Bollgard II Cotton®—Monsanto), MON88913 (FibreMax RR Flex Cotton®—Monsanto), GHB119+T304-40 (Twinlink®-BCS Stoneville), GHB119+T304-40×LL25× GHB614 (Twinlink LL GT®-BCS Stoneville), 3006-210-23×281-24-236 (PhytoGen Widestrike Insect Protection®—Dow), 3006-210-23×281-24-236×MON88913 (PhytoGen Widestrike Insect Protection+RR FLEX—® Dow/Monsanto), 3006-210-23×281-24-236×MON1445 ((PhytoGen Widestrike Insect Protection+RR®—Dow/Monsanto), MON1445 (PhytoGen Roundup Ready®—Monsanto), MON88913 (PhytoGen Roundup Ready FLEX®—Monsanto), COT102×COT67B (Vipcot®—Syngenta), COT102× COT67B—MON88913 (Vipcot RR FLEX®—Syngenta/Monsanto), 281-24-236 (Dow), 3006-210-23 (Dow), COT102 (Syngenta), COT67B (Syngenta), T304-40 (BCS Stoneville).

Examples of Soy transgenic events include MON87701× MON89788 (Genuity Roundup ready 2 Yield Soybeans®—Monsanto), MON89788 (Roundup Ready2Yield®, RR2Y®—Monsanto), MON87708 (Monsanto), 40-3-2 (Roundup Ready®, RR1®—Monsanto), MON87701 (Monsanto), DAS-68416 (Enlist Weed Control System®—Dow), DP356043 (Optimum GAT®—Pioneer), A5547-127 (LibertyLink Soybean®-Bayercropscience), A2704-12 (Bayercropscience), GU262 (Bayercropscience), W62 W98 (Bayercropscience), CRV127 (Cultivance®-BASF/EMBRAPA), SYHT0H2 (WO 2012/082548).

Examples of Maize transgenic events include T25 (LibertyLink®, LL®-Bayerscropscience), DHT-1 (Dow), TC1507 (Herculex I®—Dow), DAS59122-7 (Herculex RW®—Dow), TC1507+DAS59122-7—Herculex Xtra®—Dow), TC1507×DAS-59122-7×NK603 (Herculex Xtra+RR®—Dow), TC1507×DAS-59122-×MON88017×MON89034 (Genuity Smartstax Corn®, Genuity Smartstax RIB Complete®—Monsanto/Dow), MON89034×NK603 (Genuity VT double PRO®—Monsanto), MON89034+MON88017 (Genuity VT Triple PRO®—Monsanto), NK603 (Roundup Ready 2®, RR2®—Monsanto), MON810 (YieldGard BT®, Yieldgard Cornborer®—Monsanto), MON810×NK603 (YieldGard cornborer RR Corn 2®—Monsanto), MON810× MON863 (YieldGard Plus®—Monsanto), MON863× MON810×NK603 (YieldGard Plus+RR Corn2®/YieldGard RR Maize®—Monsanto), MON863×NK603 (YieldGard Rotworm+RR Corn 2®—Monsanto), MON863 (YieldGard RW®—Monsanto), MON89034 (YieldGard RW®—Monsanto), MON88017 (YieldGard VT RW®—Monsanto), MON810+MON88017 (YieldGard VT Triple®—Monsanto), MON88017+MON89034 (YieldGard VT Triple Pro®—Monsanto), Bt11+MIR604+GA21 (Agrisure 3000®—Syngenta), Bt11+TC1507+MIR604+5307+GA21 (Syngenta), Bt11+TC1507+MIR604+DAS59122+GA21 (Agrisure 3122®—Syngenta), BT11 (Agrisure CB®—Syngenta), GA21—(Agrisure GT®—Syngenta), MIR604 (Agrisure RW®—Syngenta), Bt11+MIR162 (Agrisure TL VIP®—Syngenta), BT11+MIR162+GA21 (Agrisure Viptra 3110®—Syngenta), BT11+MIR162+MIR604 (Agrisure TM 3100®—Syngenta), Event3272+BT11+MIR604+GA21 (Syngenta), BT11+MIR1692+MIR604+GA21 (Agrisure Viptera 3111®—Syngenta), BT11+MIR 162+TC1507+ GA21 (Agrisure Viptera 3220®—Syngenta), BT11+ MIR162+TC1507+MIR604+5307+GA21 (Agrisure Viptera 3222®—Syngenta), MIR162 (Syngenta), BT11+GA21+ MIR162+MIR604+5307 (Syngenta), 5307 (Syngenta).

Herbicide-resistant plants (plants bred in a conventional manner for herbicide tolerance) which may be mentioned include the varieties sold under the name Clearfield(®) (for example maize).

These statements also apply to plant cultivars having these genetic traits or genetic traits still to be developed, which plant cultivars will be developed and/or marketed in the future.

The compounds of the invention are suitable for use on any cotton plant, including those that have been genetically modified to be resistant to active ingredients such as herbicides, or to produce biologically active compounds that control infestation by plant pests, e.g. BT cotton.

A compound of the invention may be used in mixtures with fertilizers (for example nitrogen-, potassium- or phosphorus-containing fertilizers). Suitable formulation types include granules of fertilizer. The mixtures preferably contain up to 25% by weight of the compound of the invention.

The invention therefore also provides a fertilizer composition comprising a fertilizer and a compound of the invention.

The compositions of this invention may contain other compounds having biological activity, for example micronutrients or compounds having fungicidal activity or which possess plant growth regulating, herbicidal, insecticidal, nematicidal or acaricidal activity.

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, e.g. a insecticide, fungicide or herbicide, or a synergist or plant growth regulator where appropriate. An additional active ingredient may provide a composition having a broader spectrum of activity or increased persistence at a locus; synergize the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin and gamma cyhalothrin), bifenthrin, fenpropathrin, cyfluthrin, tefluthrin, fish safe pyrethroids (for example ethofenprox), natural pyrethrin, tetramethrin, S-bioallethrin, fenfluthrin, prallethrin, acrinathirin, etofenprox or 5-benzyl-3-furylmethyl-($\underline{E}$)-(1R,3S)-2,2-dimethyl-3-(2-oxothiolan-3-ylidenemethyl)cyclopropane carboxylate;

b) Organophosphates, such as profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron, diafenthiuron, lufeneron, novaluron, noviflumuron or chlorfluazuron;

e) Organic tin compounds, such as cyhexatin, fenbutatin oxide or azocyclotin;

f) Pyrazoles, such as tebufenpyrad, tolfenpyrad, ethiprole, pyriprole, fipronil, and fenpyroximate;
g) Macrolides, such as avermectins or milbemycins, for example abamectin, emamectin benzoate, ivermectin, milbemycin, spinosad, azadirachtin, milbemectin, lepimectin or spinetoram;
h) Hormones or pheromones;
i) Organochlorine compounds, such as endosulfan (in particular alpha-endosulfan), benzene hexachloride, DDT, chlordane or dieldrin;
j) Amidines, such as chlordimeform or amitraz;
k) Fumigant agents, such as chloropicrin, dichloropropane, methyl bromide or metam;
l) Neonicotinoid compounds, such as imidacloprid, thiacloprid, acetamiprid, nitenpyram, dinotefuran, thiamethoxam, clothianidin, or nithiazine;
m) Diacylhydrazines, such as tebufenozide, chromafenozide or methoxyfenozide;
n) Diphenyl ethers, such as diofenolan or pyriproxifen;
o) Ureas such as Indoxacarb or metaflumizone;
p) Ketoenols, such as Spirotetramat, spirodiclofen or spiromesifen;
q) Diamides, such as flubendiamide, chlorantraniliprole (Rynaxypyr®) or cyantraniliprole;
r) Essential oils such as Bugoil®—(PlantImpact); or
s) a compound selected from buprofezine, flonicamid, acequinocyl, bifenazate, cyenopyrafen, cyflumetofen, etoxazole, flometoquin, fluacrypyrim, fluensulfone, flufenerim, flupyradifuone, harpin, iodomethane, dodecadienol, pyridaben, pyridalyl, pyrimidifen, flupyradifurone, 4-[(6-Chloro-pyridin-3-ylmethyl)-(2,2-difluoro-ethyl)-amino]-5H-furan-2-one (DE 102006015467), CAS: 915972-17-7 (WO 2006/129714; WO 2011/147953; WO 2011/147952), CAS: 26914-55-8 (WO 2007/020986), chlorfenapyr, pymetrozine, sulfoxaflor and pyrifluqinazon.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorbenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxy-iminoacetamide (SSF-129), 4-bromo-2-cyano-N,N-dimethyl-6-trifluoromethylbenzimidazole-1-sulfonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy) propionamide (AC382042), N-(2-methoxy-5-pyridyl)-cyclopropane carboxamide, acibenzolar (CGA245704) (e.g. acibenzolar-S-methyl), alanycarb, aldimorph, anilazine, azaconazole, azoxystrobin, benalaxyl, benomyl, benthiavalicarb, biloxazol, bitertanol, bixafen, blasticidin S, boscalid, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulfate, copper tallate and Bordeaux mixture, cyclufenamid, cymoxanil, cyproconazole, cyprodinil, debacarb, di-2-pyridyl disulfide 1,1'-dioxide, dichlofluanid, diclomezine, dicloran, diethofencarb, difenoconazole, difenzoquat, diflumetorim, O,O-di-iso-propyl-S-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl-(Z)-N-benzyl-N-([methyl(methyl-thioethylideneamino-oxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluopyram, fluoxastrobin, fluoroimide, fluquinconazole, flusilazole, flutolanil, flutriafol, fluxapyroxad, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, isopyrazam, kasugamycin, kresoxim-methyl, LY186054, LY211795, LY248908, mancozeb, mandipropamid, maneb, mefenoxam, metalaxyl, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, penflufen, penthiopyrad, phenazin oxide, phosetyl-Al, phosphorus acids, phthalide, picoxystrobin (ZA1963), polyoxinD, polyram, probenazole, prochloraz, procymidone, propamocarb, propiconazole, propineb, propionic acid, prothioconazole, pyrazophos, pyrifenox, pyrimethanil, pyraclostrobin, pyroquilon, pyroxyfur, pyrrolnitrin, quaternary ammonium compounds, quinomethionate, quinoxyfen, quintozene, sedaxane, sipconazole (F-155), sodium pentachlorophenate, spiroxamine, streptomycin, sulfur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram, N-[9-(dichloromethylene)-1,2,3,4-tetrahydro-1,4-methanonaphthalen-5-yl]-3-(difluoromethyl)-1-methyl-1H-pyrazole-4-carboxamide [1072957-71-1], 1-methyl-3-difluoromethyl-1H-pyrazole-4-carboxylic acid (2-dichloromethylene-3-ethyl-1-methyl-indan-4-yl)-amide, and 1-methyl-3-difluoromethyl-4H-pyrazole-4-carboxylic acid [2-(2,4-dichloro-phenyl)-2-methoxy-1-methyl-ethyl]-amide.

In addition, biological agents may be included in the composition of the invention e.g. *Bacillus* species such as *Bacillus firmus, Bacillus cereus, Bacillus subtilis*, and *Pasteuria* species such as *Pasteuria penetrans* and *Pasteuria nishizawae*. A suitable *Bacillus firmus* strain is strain CNCM 1-1582 which is commercially available as BioNem™. A suitable *Bacillus cereus* strain is strain CNCM 1-1562. Of both *Bacillus* strains more details can be found in U.S. Pat. No. 6,406,690. Other biological organisms that may be included in the compositions of the invention are bacteria such as *Streptomyces* spp.

such as *S. avermitilis*, and fungi such as *Pochonia* spp. such as *P. chlamydosporia*. Also of interest are *Metarhizium* spp. such as *M. anisopliae*; *Pochonia* spp. such as *P. chlamydosporia*.

The compounds of the invention may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

Unless otherwise stated the weight ratio of the compound of I with an additional active ingredient may generally be between 1000:1 and 1:1000. In other embodiments that weight ratio of A to B may be between 500:1 to 1:500, for example between 100:1 to 1:100, for example between 1:50 to 50:1, for example 1:20 to 20:1, for example 1:10 to 10:1, for example 1:5 to 5:1, for example 1:1, 1:2, 1:3, 1:4, 1:5, 2:1, 3:1, 4:1, or 5:1.

Mixtures with pyrethroids, in particular pymetrozine, are of particular interest for the present invention.

Compositions of the invention include those prepared by premixing prior to application, e.g. as a readymix or tankmix, or by simultaneous application or sequential application to the plant.

In order to apply a compounds of the invention as an insecticide, acaricide, nematicide or molluscicide to a pest, a locus of pest, or to a plant susceptible to attack by a pest, compounds of the invention is usually formulated into a composition which includes, in addition to the compound of the invention, a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of the invention. The composition is generally used for the control of pests such that a compound of the invention is applied at a rate of from 0.1 g to 10 kg per hectare, preferably from 1 g to 6 kg per hectare, more preferably from 1 g to 1 kg per hectare.

In one embodiment the compounds of the invention are used for pest control on cotton at 1:500 g/ha, for example 10-70 g/ha. However, it should be noted that due to the very damaging effect of the *Anthonomus grandis* (quantity and quality on yield), sprays are often very intense and at very low threshold levels and can be down to almost zero tolerance.

When used in a seed dressing, a compound of the invention is used at a rate of 0.0001 g to 10 g (for example 0.001 g or 0.05 g), preferably 0.005 g to 10 g, more preferably 0.005 g to 4 g, per kilogram of seed.

Compositions comprising a compound of the invention can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), microemulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of the invention.

Dustable powders (DP) may be prepared by mixing a compound of the invention with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of the invention with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of the invention with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of the invention and one or more powdered solid diluents or carriers, or from pre-formed blank granules by absorbing a compound of the invention (or a solution thereof, in a suitable agent) in a porous granular material (such as pumice, attapulgite clays, fuller's earth, kieselguhr, diatomaceous earths or ground corn cobs) or by adsorbing a compound of the invention (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of the invention in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of the invention in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of the invention either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of the invention is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of the invention. SCs may be prepared by ball or bead milling the solid compound of the invention in a suitable medium, optionally with one or more dispersing agents, to produce a fine particle suspension of the compound. One or more wetting agents may be included in the composition and a suspending agent may be included to reduce the rate at which the particles settle. Alternatively, a compound of the invention may be dry milled and added to water, containing agents hereinbefore described, to produce the desired end product.

Aerosol formulations comprise a compound of the invention and a suitable propellant (for example n-butane). A compound of the invention may also be dissolved or dispersed in a suitable medium (for example water or a water miscible liquid, such as n-propanol) to provide compositions for use in non-pressurized, hand-actuated spray pumps.

A compound of the invention may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of the invention and, optionally, a carrier or diluent therefor. The polymeric shell may be produced by either an interfacial polycondensation reaction or by a coacervation procedure. The compositions may provide for controlled release of the compound of the invention and they may be used for seed treatment. A compound of the invention may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of the invention). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of the invention).

A compound of the invention may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of the invention may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

A compound of the invention may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of the invention (for example 0.0001 to 10%, by weight) depending upon the purpose for which they are to be used.

The invention will now be illustrated by the following non-limiting Examples. All citations are incorporated by reference.

BIOLOGICAL EXAMPLES

TABLE A

TABLE A provides compounds of formula (Ia) wherein $X^1$, $R^1$, $R^4$ and $R^5$ have the definitions shown below.

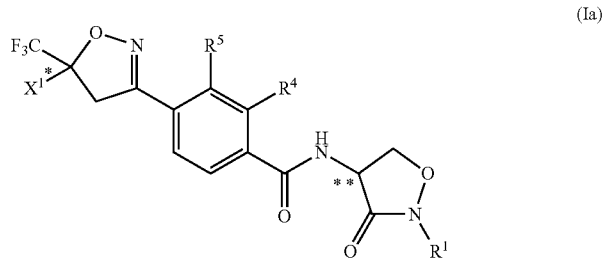

(Ia)

| | X1 | R1 | R4 | R5 | Stereo-chemistry at * | Stereo-chemistry at ** |
|---|---|---|---|---|---|---|
| A1 | 3,4,5-trichlorophenyl | 2,2,2-trifluoroethyl | CH3 | H | S | R/S |
| A2 | 3,5-dichlorophenyl | methyl | CH3 | H | S | R/S |
| A3 | 3,5-dichlorophenyl | 2,2,2-trifluoroethyl | CH3 | H | S | S |
| A4 | 3,5-dichlorophenyl | ethyl | CH3 | H | S | S |
| A5 | 3,5-dichloro-4-fluorophenyl | Ethyl | CH3 | H | S | R/S |
| A6 | 3,5-dichlorophenyl | 2,2-difluoroethyl | CH3 | H | S | R/S |
| A8 | 3,5-dichlorophenyl | 2,2,2-trifluoroethyl | CH3 | H | S | R/S |
| A9 | 3,5-dichlorophenyl | ethyl | CH3 | H | S | R/S |
| A10 | 3-chloro-5-bromophenyl | 2,2,2-trifluoroethyl | CH3 | H | R/S | R |
| A11 | 3-chloro-5-bromophenyl | ethyl | CH3 | H | R/S | R/S |
| A12 | 3-chloro-5-trifluoromethyl-phenyl | ethyl | CH3 | H | R/S | R/S |
| A14 | 3,5-dichlorophenyl | 2,2-difluoroethyl | CH3 | H | S | R |
| A15 | 3,5-trifluoromethyl-4-chlorophenyl | ethyl | CH3 | H | R/S | S |
| A16 | 3,5-dichlorophenyl | 2,2,2-trifluoroethyl | CH3 | H | S | R |

TABLE A-continued

TABLE A provides compounds of formula (Ia) wherein $X^1$, $R^1$, $R^4$ and $R^5$ have the definitions shown below.

(Ia)

| | X1 | R1 | R4 | R5 | Stereo-chemistry at * | Stereo-chemistry at ** |
|---|---|---|---|---|---|---|
| A17 | 3,5-dichlorophenyl | ethyl | CH3 | H | S | R |
| A18 | 3-chloro-5-trifluoromethyl-phenyl | ethyl | CH=CH—CH=CH | | S | R |
| A19 | 3,5-dichloro-4-fluorophenyl | ethyl | Cl | H | S | R |
| A20 | 3,5-dichloro-4-fluorophenyl | ethyl | CH3 | H | S | R |
| A21 | 3,5-dichlorophenyl | 2,2,2-trifluoroethyl | CH3 | H | R/S | R |

R/S indicates a racemic mixture.

TABLE B

Table B provides compounds of formula (Ib) wherein $X^1$ and $R^1$ have the definitions shown below.

(Ib)

| | X1 | R1 | Stereo-chemistry at * | Stereo-chemistry at ** |
|---|---|---|---|---|
| A7 | 3,5-dichlorophenyl | ethyl | R/S | S |
| A13 | 3,5-dichlorophenyl | 2,2,2-trifluoroethyl | R/S | R/S |

*Anthonomus grandis* (Cotton Boll Weevil)

Cotton plants are treated (100 mL spray volume) and 10 adult weevils are added to each plant (2 replicates per concentration). 5 days after infestation the mortality is assessed. The compounds shown in the table below were tested

| Compound | Application rate/ppm | Control/% |
|---|---|---|
| A1 | 50 | 95 |
| | 12.5 | 100 |
| | 3 | 100 |
| | 0.8 | 90 |
| | 0.2 | 45 |
| A2 | 50 | 100 |
| | 12.5 | 100 |
| | 3 | 100 |
| | 0.8 | 80 |
| | 0.2 | 45 |
| A3 | 50 | 100 |
| | 12.5 | 100 |
| | 3 | 100 |
| | 0.8 | 60 |
| | 0.2 | 60 |
| A5 | 50 | 100 |
| | 12.5 | 100 |
| | 3 | 95 |
| | 0.8 | 40 |
| | 0.2 | 40 |
| A6 | 3 | 100 |
| | 0.8 | 100 |
| | 0.2 | 95 |
| | 0.05 | 50 |
| | 0.01 | 35 |
| A8 | 3 | 100 |
| | 0.8 | 100 |
| | 0.2 | 70 |
| | 0.05 | 35 |
| | 0.01 | 20 |
| A9 | 50 | 100 |
| | 12.5 | 100 |
| | 3 | 75 |
| | 0.8 | 15 |
| | 0.2 | 25 |
| A16 | 3 | 100 |
| | 0.8 | 100 |
| | 0.2 | 100 |
| | 0.05 | 55 |
| | 0.01 | 0 |
| A17 | 50 | 100 |
| | 12.5 | 100 |
| | 3 | 100 |
| | 0.8 | 50 |
| | 0.2 | 20 |

| Compound | Application rate/ppm | Control/% |
|---|---|---|
| A18 | 50 | 100 |
| | 12.5 | 35 |
| | 3 | 30 |
| | 0.8 | 40 |
| | 0.2 | 0 |
| A19 | 50 | 100 |
| | 12.5 | 95 |
| | 3 | 85 |
| | 0.8 | 30 |
| | 0.2 | 60 |
| A20 | 50 | 100 |
| | 12.5 | 100 |
| | 3 | 100 |
| | 0.8 | 60 |
| | 0.2 | 15 |
| A21 | 50 | 100 |
| | 12.5 | 100 |
| | 3 | 100 |
| | 0.8 | 100 |
| | 0.2 | 70 |

COMPARATIVE EXAMPLE

Compounds are tested according to the above method. The results show that the compounds of the invention are significantly more active against *Anthonomus grandis* than structurally similar compounds, particularly at low rates of application.

| Compound | Test | Application rate/ppm | Control/% |
|---|---|---|---|
| Compound of the invention | *Anthonomus grandis* (Cotton boll weevil) | 12.5 | 100 |
| | | 3 | 100 |
| | | 0.8 | 100 |
| Reference compound | *Anthonomus grandis* (Cotton boll weevil) | 12.5 | 30 |
| | | 3 | 30 |
| | | 0.8 | 10 |

Compound of the invention
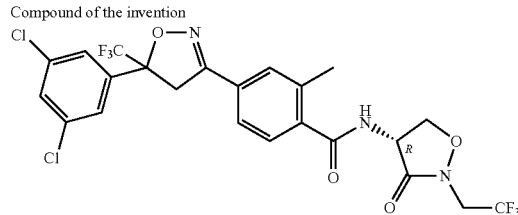

Reference compound
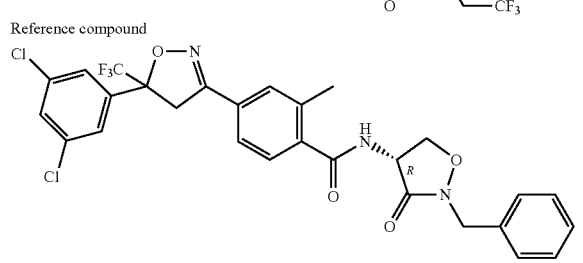

The compound of the invention and reference compound are compounds B5 and B4 respectively from WO 2011/067272.

The invention claimed is:
1. A method for controlling and/or preventing infestation of insects, the method comprising applying to a crop of cotton plants, the locus thereof, or propagation material thereof, a compound of formula (Ia) or (Ib)

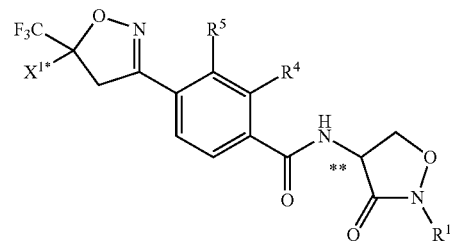

(Ia)

wherein $X^1$, $R^1$, $R^4$ and $R^5$ in the compound of formula (Ia) have the following definitions

| | X1 | R1 | R4 | R5 | Stereo-chemistry at ** | Stereo-chemistry at * |
|---|---|---|---|---|---|---|
| A1 | 3,4,5-trichloro-phenyl | 2,2,2-tri-fluoro-ethyl | CH3 | H | S | R/S |
| A5 | 3 5-dichloro-4-fluoro-phenyl | Ethyl | CH3 | H | S | R/S |
| A10 | 3-chloro-5-bromo-phenyl- | 2,2,2-tri-fluoro-ethyl | CH3 | H | R/S | R |
| A11 | 3-chloro-5-bromo-phenyl | ethyl | CH3 | H | R/S | R/S |
| A12 | 3-chloro-5-trifluoro-methyl-phenyl | ethyl | CH3 | H | R/S | R/S |
| A14 | 3,5-dichloro-phenyl | 2,2-di-fluoro-ethyl | CH3 | H | S | R |
| A15 | 3,5-trifluoro-methyl-4-chloro-phenyl | ethyl | CH3 | H | R/S | S |
| A18 | 3-chloro-5-trifluoro-methyl-phenyl | ethyl | CH=CH—CH=CH | | S | R |
| A19 | 3 5-di-chloro-4-fluorophenyl | ethyl | Cl | H | S | R |
| A20 | 3 5-di-chloro-4-fluorophenyl | ethyl | CH3 | H | S | R | and R/S indicates a racemic mixture, or a compound of formula (Ib)

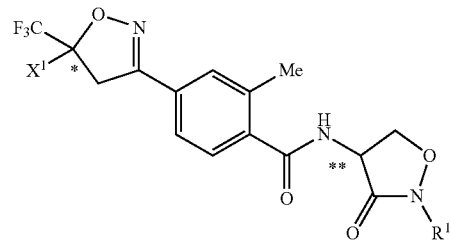

(Ib)

wherein $X^1$ and $R^1$ in the compound of formula (Ib) have the following definitions

|     | X1                | R1                  | Stereochemistry at * | Stereochemistry at ** |
|-----|-------------------|---------------------|----------------------|-----------------------|
| A7  | 3,5-dichlorophenyl | ethyl              | R/S                  | S                     |
| A13 | 3,5-dichlorophenyl | 2,2,2-trifluoroethyl | R/S                  | R/S                   | and R/S indicates a racemic mixture.

2. A method according to claim 1, wherein the method is a method of controlling and/or preventing infestation of insects the family Curculionidae in cotton comprising applying to a crop of cotton plants, the locus thereof, or propagation material thereof.

3. A method according to claim 2, wherein said insects are selected from the group consisting of a member of the genus *Anthonomus* and *Anthonomus grandis*.

4. A method according to claim 3, wherein said insects are selected from the group consisting of *Anthonomus corvulus, Anthonomus elutus, Anthonomus elongatus, Anthonomus eugenii, Anthonomus consors, Anthonomus haematopus, Anthonomus lecontei, Anthonomus molochinus, Anthonomus morticinus, Anthonomus musculus, Anthonomus nigrinus, Anthonomus phyllocola, Anthonomus pictus, Anthonomus pomorum, Anthonomus quadrigibbus, Anthonomus rectirostris, Anthonomus rubi, Anthonomus santacruzi, Anthonomus signatus, Anthonomus subfasciatus,* and *Anthonomus tenebrosus*.

5. A method of protecting by controlling and/or preventing insect/pest infestation on a plot of at least five hectares comprising a crop of useful plants, susceptible to and/or under attack by insects/pests, including at one least insects/pests selected from a member of the family Curculionidae and *Anthonomus grandis*, said method comprising applying to said plant and/or said insects/pests a compound of formula (Ia) or formula (Ib) as defined in claim 1 in a pre-defined plot part that is between 0.5 to 20%, based on area, of the plot, provided said pre-defined plot part forms the outer border of the plot, wherein said insects/pests predominantly approach the plot from the periphery of the plot.

\* \* \* \* \*